(12) United States Patent
Beaulieu et al.

(10) Patent No.: US 7,380,468 B2
(45) Date of Patent: Jun. 3, 2008

(54) DEVICE FOR INTEGRATING ELECTRODES CHARACTERIZING THE FLOW OF A MULTIPHASE FLUID IN A TUBING

(75) Inventors: Jean-Philippe Beaulieu, Montreuil (FR); Jean-Luc Garcia, Courcouronnes (FR); Jean-Pierre Moenner, Chatillon (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/501,027

(22) PCT Filed: Dec. 20, 2002

(86) PCT No.: PCT/EP02/14822

§ 371 (c)(1),
(2), (4) Date: Mar. 9, 2006

(87) PCT Pub. No.: WO03/058225

PCT Pub. Date: Jul. 17, 2003

(65) Prior Publication Data

US 2006/0158192 A1 Jul. 20, 2006

(30) Foreign Application Priority Data

Jan. 11, 2002 (FR) .................................. 02 00308

(51) Int. Cl.
*G01F 1/58* (2006.01)
*G01F 1/86* (2006.01)
*G01F 1/56* (2006.01)

(52) U.S. Cl. ............................... 73/861.12; 73/861.02; 73/861.08

(58) Field of Classification Search .............. 73/861.12
See application file for complete search history.

(56) References Cited

U.S. PATENT DOCUMENTS

| | | | | |
|---|---|---|---|---|
| 4,513,624 A * | 4/1985 | McHale et al. ........... | 73/861.12 |
| 4,741,215 A * | 5/1988 | Bohn et al. .............. | 73/861.12 |
| 4,912,838 A * | 4/1990 | Goto et al. ................ | 29/602.1 |
| 5,280,727 A * | 1/1994 | Hafner et al. ............ | 73/861.12 |
| 5,307,687 A * | 5/1994 | Arai et al. ............... | 73/861.12 |
| 5,398,553 A * | 3/1995 | Hemp ...................... | 73/861.15 |
| 5,750,902 A * | 5/1998 | Schwiderski .............. | 73/861.12 |
| 6,802,223 B2 * | 10/2004 | Nakatani et al. .......... | 73/861.12 |
| 6,983,661 B2 * | 1/2006 | Zingg ...................... | 73/861.12 |

* cited by examiner

*Primary Examiner*—Harshad Patel
(74) *Attorney, Agent, or Firm*—Matthias Abrell; Bryan L. White; Darla Fonseca

(57) ABSTRACT

The invention relates to a device for integrating electrodes (12) characterizing the flow of a multiphase fluid in a tubing (10). The device includes a tube section (14) made out of an electrically insulating material and bearing the electrodes on its external surface. A metal compensation sheath (16) encircles the section (14), being separated from the latter by an insulating and incompressible fluid. An annular chamber (18) outside the sheath communicates with the inside of the tubing (10). The sheath (16) is fixed on seal rings (29) inserted at the ends of the section (14), by reinforcement for example.

10 Claims, 1 Drawing Sheet

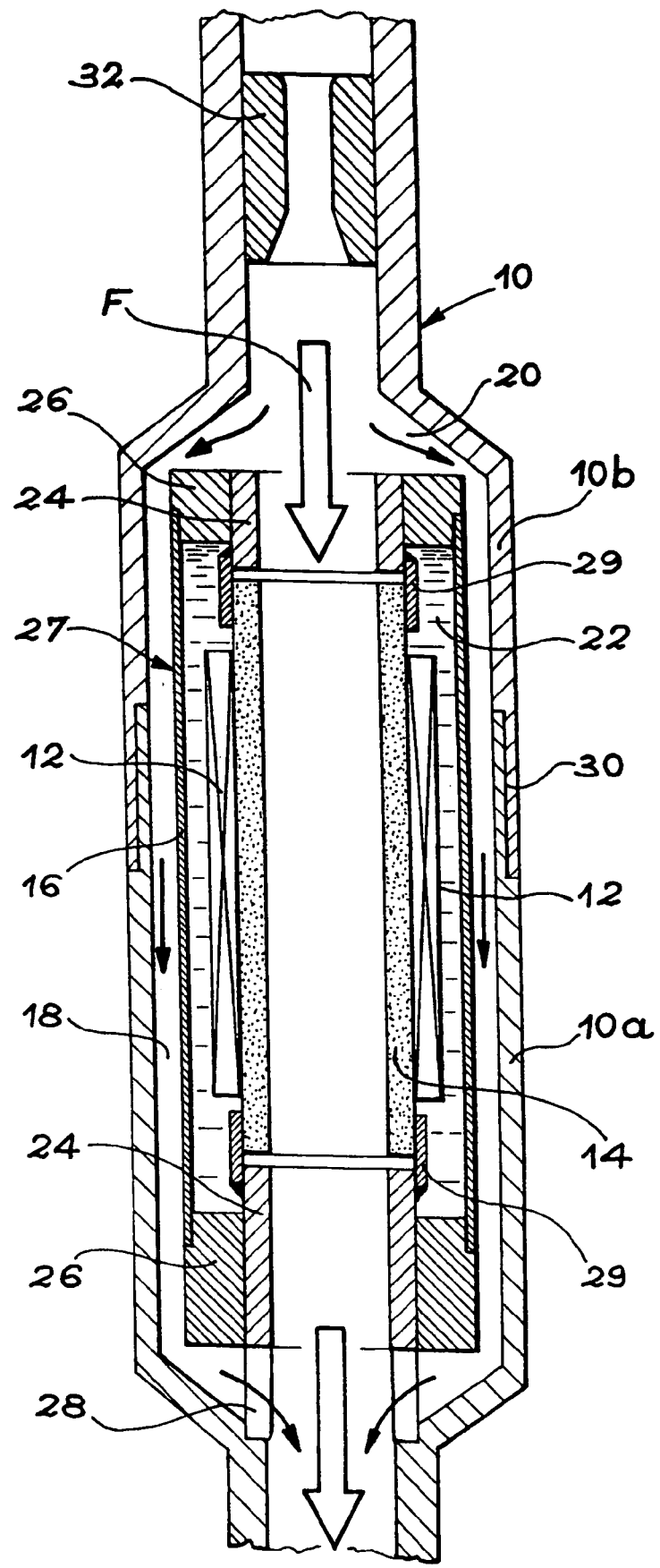

DEVICE FOR INTEGRATING ELECTRODES CHARACTERIZING THE FLOW OF A MULTIPHASE FLUID IN A TUBING

FIELD OF THE INVENTION

The invention relates to a device for integrating in a tubing, such as a tubing in an oil well, electrodes used for characterizing the flow of a multiphase fluid in the tubing.

BACKGROUND OF THE INVENTION

A device for characterizing the flow of a multiphase fluid flowing inside a tubing is described in documents FR-A-2 780 499 and FR-A-2 806 799. This device comprises several sets of electrodes positioned on the tubing, in such a way that the fluid flows between the electrodes. In such a device, the electrodes measure very weak currents and impedances. They should therefore not be in direct contact with the fluid and should be electrically insulated from the tubing. In addition, the fluid should be confined to flow through the middle of the group of electrodes. Therefore the latter should be an integral part of the tubing. However, the tubing in which measurements are performed often operate in environments such as are found in oil wells in which particularly harsh conditions prevail. For example, the temperature may attain several hundred degrees and the pressure may be larger than 1,000 bar in an environment containing $H_2S$. The device for integrating the electrodes into the tubing should there fore withstand such conditions without reducing the internal diameter of the tubing.

SUMMARY OF THE INVENTION

The present invention provides a device for integrating electrodes for characterizing the flow of a multiphase fluid into a tubing, by preventing any direct contact between the fluid and the electrodes and by providing electric insulation of the latter with respect to the tubing. The invention is characterized in that it comprises a tube section made out of an electrically insulating material and having an internal diameter substantially equal to that of the tubing, tube section being integrated in the tubing and bearing the electrodes on its external surface.

With this layout, the electrical insulation of the electrodes with respect to the tubing may be ensured and any direct contact between the electrodes and the fluid which flows in the tubing may be prevented.

In a preferred embodiment of the invention, a flexible compensation sheath encircles the tube section bearing the electrodes, by delimiting with this section a first annular closed space, filled with an insulating and incompressible fluid and by delimiting with a portion of the tubing encircling the sheath a second annular space which communicates with the fluid flowing in the tubing. With this layout, the tube section bearing the electrodes may be protected from the pressure which prevails within the tubing, by maintaining this tube section in equipressure. Indeed, the pressure inside the tubing may be larger than 1,000 bar when the device is implemented at the bottom of a well.

In this preferred embodiment of the invention, seal rings are advantageously sealably secured on the ends of the tube section bearing the electrodes. The tube section is thus connected to the compensation sheath by gas-proof gaskets, able to withstand a pressure differential of about 10 bar.

Preferably, the flexible compensation sheath is a metal sheath with ends welded onto metal rings, themselves welded on intermediate metal rings to which are welded seal rings.

In the preferred embodiment of the invention, the seal rings are advantageously sealably secured on the ends of the tube section bearing the electrodes, by a securing arrangement such as reinforcement, O-rings or bonding.

Preferably, the tube section bearing the electrodes forms, together with the compensation sheath and the seal rings, a sensor assembly which is mounted inside a junction area between two tubing sections. The sensor assembly may then be flexibly mounted within the junction area, by interposition of elastic mountings. The junction area integrates mountings for joining both sections of the tubing, such as making up or welding.

Advantageously, the measurement is performed in the area of the tubing within which the fluid is homogeneous. For this purpose, a mixing system such as a Venturi is placed in the tubing, upstream from the tube section bearing the electrodes.

Preferably, the Venturi has then an internal diameter less than half of the internal diameter of the tubing and the distance between the outlet end of the Venturi and the inlet end of the tube section bearing the sensors is between 1 and 10 times the internal diameter of the tubing.

Finally, the tube section bearing the electrodes is advantageously made out of a material selected from the group comprising plastics, rubber derivatives, polymers, and ceramics.

DETAILED DESCRIPTION

As an illustrative and non-limiting example, a preferred embodiment of the invention will now be described, with reference to the appended drawing, wherein the single figure is a longitudinal sectional view which illustrates a device for integrating electrodes characterizing the flow of a multiphase fluid in a tubing, according to the invention.

In the single FIGURE, reference number 10 generally refers to a tubing placed inside the casing (not shown) of an oil well. The tubing 10 pipelines the flow of a multiphase fluid generally formed by an immiscible mixture of liquid petroleum, petroleum gas and water. This flow is symbolized by the arrow F in the FIGURE.

As taught by documents FR-A-2 780 499 and FR-A-2 806 799, it is known how to characterize the flow of the fluid in the tubing 10 by means of several sets of electrodes positioned on the tubing in such a way that the fluid flows between said electrodes. As explained in detail in these documents, characterization of the flow consists of a dielectric measurement and a resistive measurement of the fluid. The different sets of electrodes are illustrated at 12 in the FIGURE.

The invention relates to a device for providing mechanical integration of the electrodes 12 into the tubing 10. First, this device takes into account the physical constraints which result from the fact that the electric currents and the impedances measured by the electrodes 12 are very low. These constraints are the requirement of physically insulating the electrodes from the fluid on the one hand, i.e. preventing any direct contact between them, and on the other hand providing the electrical insulation of the electrodes 12 with respect to the tubing 10. For this purpose, the electrodes 12 are placed on a tube section 14, made out of an electrically insulating material. This material can be selected from plastics, rubber derivatives, polymers and ceramics. More specifically, the selection of the material is carried out in order to obtain the dielectric constant mentioned in documents FR-A-2 780 499 and FR-A-2 806 799 and in order that the material be sufficiently resistant to temperature, shock and corrosion, according to the expected operating conditions.

As illustrated in the FIGURE, the tube section 14 has a cylindrical shape and its internal diameter is the same as that of the tubing 10. The external diameter of the tube section 14 is calculated from the dielectric constant of the material with which it is formed, considering the fact that the thickness of the section should be sufficient for it to withstand mechanical stresses which will be applied to it during operation. Conversely, the external diameter of the tube section 14 should not be excessive, so as to allow it to be mounted within the casing of the well, considering the fact that the electrodes 12 as well as various other components which will be described later on, are placed around said tube section.

In the preferred embodiment of the device for integrating the electrodes 12 illustrated in the FIGURE, the tube section 14 is submitted to isostatic pressure, i.e. it is maintained in equipressure with respect to the pressure prevailing within the tubing 10. With this layout, the fact may be considered that the tube section 14 is made out of an insulating material for which the mechanical strength is less than that of metals, while the pressure within the tubing may attain more than 1,000 bar. The isostatic pressurization of the tube section 14 bearing the electrodes 12 is obtained by placing a compensation sheath 16 around this section and by forming around this sheath, an annular space 18, sealed with respect to the outside world and which communicates with the inside of the tubing 10 through at least one passage 20. It is understood that with this layout, a pressure substantially equal to that prevailing within the tubing 10 may be established around the tube section 14 while retaining the physical insulation of the electrodes 12 with respect to the fluid flowing in the tubing. The compensation sheath 16 must be very thin and flexible in order to properly transmit the pressure to the tube section 14. It should also be manufactured so that it does not plastically deform under the effect of the pressure. In the preferred embodiment, the compensation sheath 16 is therefore metal.

In order to notably retain the electrical insulation of the electrodes 12, while providing transmission of the prevailing pressure in the annular chamber 18 to the tube section 14, the compensation sheath 16 is separated from said tube section by an annular chamber 22 filled with an insulating and incompressible fluid such as an electrically insulating oil. The annular chamber 22 is a closed and sealed chamber.

In order to provide the seal between the electrodes 12 and the fluid of the well, contained in the annular chamber 18, the ends of the compensation sheath 16 are welded. Considering the fact that the tube section 14 is not metal, the ends of the compensation sheath are welded onto metal rings 26, themselves welded to intermediate rings 24, which are welded to seal rings 29, themselves sealably secured to the ends of the tube section 14. The manner in which by which the seal rings 29 are secured to the ends of the tube section 14 is selected by taking into account the different nature of the materials to be assembled, so that the fittings are gas-proof under an internal pressure of several tens of bars to a few hundred degrees. Among the securing means which meet these constraints are O-rings, the use of an adhesive, brazing, molding and interference. In the described embodiment, the seal rings 29 are secured to the ends of the tube section 14 by interference. For this purpose, the seal rings 29 are machined so that their internal diameter is less, by a value calculated in order to obtain the seal, than the external diameter of the tube section 14. Machining tolerances for diameters are very strict and the surfaces are machined in order to achieve a surface finish roughness less than a few tenths of a micron. The machined seal rings 29 are then heated. This heating has the effect of expanding the rings in such a way that their internal diameter is greater than the external diameter of the tube section 14. The latter is then rapidly introduced into the rings. Upon cooling, the rings contract andapply a strong clamping force on the tube section, sufficient for providing the seal fitting under the conditions mentioned earlier.

If allowed by the shapes of the seal rings 29, the compensation sheath 16 may be directly welded on the latter. Generally and as illustrated in the FIGURE, the compensation sheath 16 is welded on spacer rings 26, themselves welded on intermediate rings 24.

The tube section 14 bearing the electrodes forms with the compensation sheath 16 and rings 29, 26 and possibly 24, a sensor assembly 27, integrated into the tubing 10. The device illustrated in the FIGURE is also designed in such a way that the tubing 10 is able to withstand in this area the same mechanical stresses as over the remainder of its length. Thus, the weight of the tubing may exert on itself a tensile force equivalent to more than 100 metric tons. The fact that the sensor assembly 27 should have the same internal diameter as the tubing 10, the requirement of being able to install the assembly in the casing and that of providing its sealing with respect to the annular passage formed between the tubing 10 and the casing, are added to this constraint. In order to meet these different constraints, the device illustrated in the single FIGURE, is made in such a way that the sensor assembly 27 is flexibly mounted within a junction area between two sections 10a and 10b of the tubing 10. With this layout, the sensor assembly 27 is not subjected to tensile or compressive stresses. This may be achieved by securing the sensor assembly 27 to the upper section 10a of the tubing 10 via an elastic system 28. The passage 20 through which the inside of the tubing 10 communicates with the annular chamber 18, is then formed between the tubing 10 and the outside of the sensor assembly 27.

The junction between the two sections 10a and 10b of the tubing 10 is provided by junction means 30 able to provide transmission of stresses, such as welding or making up.

As described in document FR-A-2 780 499 and FR-A-2 806 799, the different measurements performed by the electrodes 12 integrate dielectric measurements and resistive measurements of the fluid. The accuracy of these measurements is supported by a physical principle based on the homogeneous character of the fluid. However, the different phases of the fluid flowing in the well are not miscible. Actually, this is generally a binary mixture of liquid petroleum and water or a ternary mixture of liquid petroleum, petroleum gas and water.

In order to cause the fluid which flows within the sensor assembly 27, to have characteristics as homogeneous as possible, a mixing system is introduced inside the tubing 10, upstream from the sensor forming set 27. For example, the mixing system may be a system which generates a pressure drop such as a Venturi 32. More specifically and as schematically illustrated in the FIGURE, the Venturi 32 is placed upstream from the sensor assembly 27, the distance L between the outlet of the Venturi and the inlet of the electrodes is such that $1D<L<10D$, wherein D refers to the internal diameter of the tubing 10. Further, the internal diameter d of the Venturi 32 is such that $0.316<\beta<0.7751$, with $\beta=d/D$. With these characteristics as well as with the nature of the fluid and the flow rate, the fluid may be provided with homogeneity able to guarantee the accuracy of the performed measurements.

The invention is not limited to the preferred embodiment described. Other modes for mounting the tube section 14, which meet the mechanical and physical constraints mentioned earlier, may be adopted without departing from the scope of the invention.

The invention claimed is:

1. A device for integrating electrodes for characterizing the flow of a multiphase fluid into a tubing through which the fluid flows, comprising:
    a tube section made out of an electrically insulating material and having an internal diameter substantially equal to that of the tubing, said tube section being integrated into the tubing and bearing the electrodes on its external surface; and
    a flexible compensation sheath that encircles the tube section bearing the electrodes, the sheath delimiting, with the tube section, a first closed annular space which filled with an insulating and incompressible fluid, and with a portion of the tubing encircling the sheath, a second annular space which communicates with the fluid flowing in the tubing.

2. The device as claimed in claim 1, wherein seal rings are secured on the ends of the tube section bearing the electrodes.

3. The device as claimed in claim 2, wherein the flexible compensation sheath is an elastic membrane, the ends of which are directly or indirectly secured on the seal rings.

4. The device as claimed in claim 2, wherein the seal rings are secured on the ends of the tube section bearing the electrodes by means of interference or shrink fit, brazing, molding, O-rings, or bonding.

5. The device as claimed in claim 2, wherein the tube section bearing the electrodes forms, with the compensation sheath and the seal rings, a sensor assembly which is mounted within a junction area between two sections of the tubing.

6. The device as claimed in claim 5, wherein the sensor assembly is flexibly mounted within the junction area, with interposition of elastic mountings.

7. The device as claimed in claim 5, wherein the junction between the two sections of the tubing is threaded or welded.

8. The device as claimed in claim 1, further comprising a mixing system placed in the tubing, upstream from the tube section.

9. The device as claimed in claim 8, wherein the mixing system is a Venturi with an internal diameter d such as $0.3164<\beta<0.7751$, with $\beta=d/D$, D being the internal diameter of the tubing, and the distance between the outlet end of the Venturi and inlet end of the tube section bearing the sensors is between 1 and 10 times the internal diameter of the tube.

10. The device as claimed in claim 1, wherein the tube section made out of an electrically insulating plastic, rubber derivative, polymer or ceramic material.

* * * * *